(12) United States Patent
Moore

(10) Patent No.: US 9,814,378 B2
(45) Date of Patent: Nov. 14, 2017

(54) FULL SPECTRUM LED ILLUMINATOR HAVING A MECHANICAL ENCLOSURE AND HEATSINK

(71) Applicant: Novadaq Technologies Inc., Mississauga (CA)

(72) Inventor: Frederick Allen Moore, Vancouver (CA)

(73) Assignee: Novadaq Technologies Inc., Mississauga (CA)

(*) Notice: Subject to any disclaimer, the term of this patent is extended or adjusted under 35 U.S.C. 154(b) by 0 days.

(21) Appl. No.: 15/247,419

(22) Filed: Aug. 25, 2016

(65) Prior Publication Data
US 2016/0360956 A1 Dec. 15, 2016

Related U.S. Application Data

(63) Continuation of application No. 14/658,869, filed on Mar. 16, 2015, now Pat. No. 9,435,496, which is a
(Continued)

(51) Int. Cl.
*F21V 13/02* (2006.01)
*F21V 9/00* (2015.01)
(Continued)

(52) U.S. Cl.
CPC .............. *A61B 1/128* (2013.01); *A61B 1/063* (2013.01); *A61B 1/0638* (2013.01);
(Continued)

(58) Field of Classification Search
CPC ..... A61B 1/128; A61B 5/0071; A61B 1/0684; A61B 1/063; A61B 2090/309;
(Continued)

(56) References Cited

U.S. PATENT DOCUMENTS 1,290,744 A 1/1919 Hollander
2,453,336 A 11/1948 Orser
(Continued)

FOREIGN PATENT DOCUMENTS

CN 101726980 A 6/2010
CN 101828139 A 9/2010
(Continued)

OTHER PUBLICATIONS

US 6,692,429, 02/2004, Imaizumi et al. (withdrawn)
(Continued)

*Primary Examiner* — Tracie Y Green
(74) *Attorney, Agent, or Firm* — Morrison & Foerster, LLP

(57) ABSTRACT

An apparatus for providing a light output to an optical guide for illumination of an imaged object including a plurality of solid state light-emitting sources each of which are independently powered and independently controlled, each light-emitting source emitting light at a wavelength which is different from the wavelength emitted by the other light-emitting sources. The apparatus also includes a heat sink configured to thermally couple the plurality of solid state light-emitting sources and provide conduction of heat generated by the plurality of solid state light-emitting sources. The apparatus further includes an optical elements to collect, collimate, and combine the emissions from the plurality of solid state light-emitting sources into a combined beam of light to be optically coupled to the light guide.

13 Claims, 2 Drawing Sheets

Related U.S. Application Data continuation of application No. 13/415,561, filed on Mar. 8, 2012, now Pat. No. 8,979,301.

(60) Provisional application No. 61/450,360, filed on Mar. 8, 2011.

(51) Int. Cl.

| | | |
|---|---|---|
| *A61B 1/12* | (2006.01) | |
| *A61B 1/06* | (2006.01) | |
| *F21V 29/70* | (2015.01) | |
| *F21V 5/04* | (2006.01) | |
| *F21V 9/08* | (2006.01) | |
| *F21K 9/60* | (2016.01) | |
| *F21V 29/89* | (2015.01) | |
| *A61B 5/00* | (2006.01) | |
| *F21V 15/01* | (2006.01) | |
| *F21V 23/02* | (2006.01) | |
| *F21V 8/00* | (2006.01) | |
| *G02B 23/24* | (2006.01) | |
| F21Y 101/00 | (2016.01) | |
| F21Y 115/30 | (2016.01) | |
| F21Y 115/10 | (2016.01) | |
| F21Y 113/13 | (2016.01) | |
| A61B 90/30 | (2016.01) | |
| F21Y 103/10 | (2016.01) | |

(52) U.S. Cl.
CPC .......... *A61B 1/0684* (2013.01); *A61B 5/0071* (2013.01); *F21K 9/60* (2016.08); *F21V 5/04* (2013.01); *F21V 9/08* (2013.01); *F21V 15/01* (2013.01); *F21V 23/02* (2013.01); *F21V 29/70* (2015.01); *F21V 29/89* (2015.01); *G02B 6/0001* (2013.01); *G02B 23/2469* (2013.01); *A61B 2090/306* (2016.02); *A61B 2090/309* (2016.02); *F21Y 2101/00* (2013.01); *F21Y 2103/10* (2016.08); *F21Y 2113/13* (2016.08); *F21Y 2115/10* (2016.08); *F21Y 2115/30* (2016.08)

(58) Field of Classification Search
CPC .......... F21V 23/02; F21V 29/89; F21V 15/01; F21V 5/04; F21V 29/70; F21V 9/08; G02B 6/0001; G02B 23/2469; F21K 9/60
See application file for complete search history.

(56) References Cited

U.S. PATENT DOCUMENTS

| | | |
|---|---|---|
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,158,504 A | 6/1979 | de Ponteves et al. |
| 4,200,801 A | 4/1980 | Schuresko |
| 4,260,217 A | 4/1981 | Traeger et al. |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,638,365 A | 1/1987 | Kato |
| 4,660,982 A | 4/1987 | Okada |
| 4,688,905 A | 8/1987 | Okamura |
| 4,717,952 A | 1/1988 | Kohayakawa et al. |
| 4,742,388 A | 5/1988 | Cooper et al. |
| 4,768,513 A | 9/1988 | Suzuki |
| 4,786,813 A | 11/1988 | Svanberg et al. |
| 4,799,104 A | 1/1989 | Hosoya et al. |
| 4,806,005 A | 2/1989 | Schneider et al. |
| 4,821,117 A | 4/1989 | Sekiguchi |
| 4,837,625 A | 6/1989 | Douziech et al. |
| 4,852,985 A | 8/1989 | Fujihara et al. |
| 4,856,495 A | 8/1989 | Tohjoh et al. |
| 4,885,634 A | 12/1989 | Yabe |
| 4,895,145 A | 1/1990 | Joffe et al. |
| 4,930,516 A | 6/1990 | Alfano et al. |
| 4,930,883 A | 6/1990 | Salzman |
| 4,951,135 A | 8/1990 | Sasagawa et al. |
| 4,953,539 A | 9/1990 | Nakamura et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,134,662 A | 7/1992 | Bacus et al. |
| 5,165,079 A | 11/1992 | Schulz-Hennig |
| 5,205,280 A | 4/1993 | Dennison, Jr. et al. |
| 5,208,651 A | 5/1993 | Buican |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,282,082 A | 1/1994 | Espie et al. |
| 5,295,017 A | 3/1994 | Brown |
| RE34,622 E | 5/1994 | Ledley |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,426,530 A | 6/1995 | Copenhaver et al. |
| 5,430,476 A | 7/1995 | Häfele et al. |
| 5,481,401 A | 1/1996 | Kita et al. |
| 5,485,203 A | 1/1996 | Nakamura et al. |
| 5,490,015 A | 2/1996 | Umeyama et al. |
| 5,507,287 A | 4/1996 | Palcic et al. |
| 5,515,449 A | 5/1996 | Tsuruoka et al. |
| 5,535,052 A | 7/1996 | Jörgens |
| 5,536,236 A | 7/1996 | Yabe et al. |
| 5,557,451 A | 9/1996 | Copenhaver et al. |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,677,724 A | 10/1997 | Takizawa et al. |
| 5,682,567 A | 10/1997 | Spruck et al. |
| 5,689,354 A | 11/1997 | Orino |
| 5,695,049 A | 12/1997 | Bauman |
| 5,697,373 A | 12/1997 | Richards-Kortum et al. |
| 5,713,364 A | 2/1998 | DeBaryshe et al. |
| 5,729,382 A | 3/1998 | Morita et al. |

(56) References Cited

U.S. PATENT DOCUMENTS

| | | |
|---|---|---|
| 5,749,830 A | 5/1998 | Kaneko et al. |
| 5,769,792 A | 6/1998 | Palcic et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,838,001 A | 11/1998 | Minakuchi et al. |
| 5,840,017 A | 11/1998 | Furusawba et al. |
| 5,852,498 A | 12/1998 | Youvan et al. |
| 5,891,016 A | 4/1999 | Utsui et al. |
| 5,897,269 A | 4/1999 | Ross et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,147,705 A | 11/2000 | Krauter et al. |
| 6,148,227 A | 11/2000 | Wagnières et al. |
| 6,161,035 A | 12/2000 | Furusawa |
| 6,181,414 B1 | 1/2001 | Raz et al. |
| 6,192,267 B1 | 2/2001 | Scherninski et al. |
| 6,212,425 B1 | 4/2001 | Irion et al. |
| 6,226,126 B1 | 5/2001 | Conemac |
| 6,258,576 B1 | 7/2001 | Richards-Kortum et al. |
| 6,280,378 B1 | 8/2001 | Kazuhiro et al. |
| 6,293,911 B1 | 9/2001 | Imaizumi et al. |
| 6,315,712 B1 | 11/2001 | Rovegno |
| 6,332,092 B1 | 12/2001 | Deckert et al. |
| 6,364,829 B1 | 4/2002 | Fulghum |
| 6,364,831 B1 | 4/2002 | Crowley |
| 6,419,628 B1 | 7/2002 | Rudischhauser et al. |
| 6,422,994 B1 | 7/2002 | Kaneko et al. |
| 6,462,770 B1 | 10/2002 | Cline et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schäfer et al. |
| 6,571,119 B2 | 5/2003 | Hayashi |
| 6,596,996 B1 | 7/2003 | Stone et al. |
| 6,603,552 B1 | 8/2003 | Cline et al. |
| 6,639,664 B2 | 10/2003 | Haan et al. |
| 6,652,452 B1 | 11/2003 | Seifert et al. |
| 6,750,971 B2 | 6/2004 | Overbeck et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,826,424 B1 | 11/2004 | Zeng et al. |
| 6,898,458 B2 | 5/2005 | Zeng et al. |
| 6,899,675 B2 | 5/2005 | Cline et al. |
| 6,922,583 B1 | 7/2005 | Perelman et al. |
| 6,960,165 B2 | 11/2005 | Ueno et al. |
| 7,043,291 B2 | 5/2006 | Sendai |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| 7,385,772 B2 | 6/2008 | Forkey et al. |
| 7,420,151 B2 | 9/2008 | Fengler et al. |
| 7,479,990 B2 | 1/2009 | Imaizumi et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,798,955 B2 | 9/2010 | Ishihara et al. |
| 7,811,229 B2 | 10/2010 | Sugimoto |
| 8,140,147 B2 | 3/2012 | Maynard et al. |
| 8,285,015 B2 | 10/2012 | Demos |
| 8,337,400 B2 | 12/2012 | Mizuyoshi |
| 8,361,775 B2 | 1/2013 | Flower |
| 8,408,269 B2 | 4/2013 | Fengler et al. |
| 8,408,772 B2 | 4/2013 | Li |
| 8,448,867 B2 | 5/2013 | Liu et al. |
| 8,498,695 B2 | 7/2013 | Westwick et al. |
| 8,630,698 B2 | 1/2014 | Fengler et al. |
| 8,759,243 B2 | 6/2014 | Coffy et al. |
| 8,773,756 B2 | 7/2014 | Tesar et al. |
| 8,790,253 B2 | 7/2014 | Sunagawa et al. |
| 8,961,403 B2 | 2/2015 | Cline et al. |
| 8,979,301 B2 * | 3/2015 | Moore .................. A61B 1/063 362/228 |
| 9,143,746 B2 | 9/2015 | Westwick et al. |
| 9,173,554 B2 | 11/2015 | Fengler et al. |
| 9,295,392 B2 | 3/2016 | Douplik et al. |
| 9,386,909 B2 | 7/2016 | Fengler et al. |
| 9,435,496 B2 * | 9/2016 | Moore .................. A61B 1/063 |
| 9,642,532 B2 | 5/2017 | Fengler et al. |
| 2001/0016679 A1 | 8/2001 | Futatsugi et al. |
| 2001/0028458 A1 | 10/2001 | Xiao |
| 2001/0049473 A1 | 12/2001 | Hayashi |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0035330 A1 | 3/2002 | Cline et al. |
| 2002/0076480 A1 | 6/2002 | Hsieh et al. |
| 2002/0138008 A1 | 9/2002 | Tsujita et al. |
| 2002/0143243 A1 | 10/2002 | Georgakoudi et al. |
| 2002/0155619 A1 | 10/2002 | Kurihara et al. |
| 2002/0161282 A1 | 10/2002 | Fulghum |
| 2002/0161283 A1 | 10/2002 | Sendai |
| 2002/0161284 A1 | 10/2002 | Tanaka |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2002/0196335 A1 | 12/2002 | Ozawa |
| 2003/0002036 A1 | 1/2003 | Haan et al. |
| 2003/0042493 A1 | 3/2003 | Kazakevich |
| 2003/0117491 A1 | 6/2003 | Avni et al. |
| 2003/0135092 A1 | 7/2003 | Cline et al. |
| 2003/0153811 A1 | 8/2003 | Muckner |
| 2003/0191368 A1 | 10/2003 | Wang et al. |
| 2003/0229270 A1 | 12/2003 | Suzuki et al. |
| 2004/0006276 A1 | 1/2004 | Demos et al. |
| 2004/0010183 A1 | 1/2004 | Dhindsa |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0133073 A1 | 7/2004 | Berci et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0186351 A1 | 9/2004 | Imaizumi et al. |
| 2004/0218115 A1 | 11/2004 | Kawana et al. |
| 2004/0225222 A1 | 11/2004 | Zeng et al. |
| 2004/0245350 A1 | 12/2004 | Zeng |
| 2004/0263643 A1 | 12/2004 | Imaizumi et al. |
| 2005/0027166 A1 | 2/2005 | Matsumoto et al. |
| 2005/0096505 A1 | 5/2005 | Imaizumi et al. |
| 2005/0140270 A1 | 6/2005 | Henson et al. |
| 2005/0143627 A1 | 6/2005 | Cline et al. |

(56) References Cited

U.S. PATENT DOCUMENTS

| | | |
|---|---|---|
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0203421 A1 | 9/2005 | Zeng et al. |
| 2005/0256373 A1 | 11/2005 | Bar-Or et al. |
| 2005/0273011 A1 | 12/2005 | Hattery et al. |
| 2005/0280783 A1 | 12/2005 | Yamasaki et al. |
| 2005/0288593 A1 | 12/2005 | Georgakoudi et al. |
| 2006/0002141 A1 | 1/2006 | Ouderkirk et al. |
| 2006/0004292 A1 | 1/2006 | Beylin |
| 2006/0017913 A1 | 1/2006 | Kawamata et al. |
| 2006/0089554 A1 | 4/2006 | Ishihara et al. |
| 2006/0146322 A1 | 7/2006 | Komachi et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0241496 A1 | 10/2006 | Fengler et al. |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0177152 A1 | 8/2007 | Tearney et al. |
| 2007/0213593 A1 | 9/2007 | Nakaoka |
| 2007/0229309 A1 | 10/2007 | Tomita et al. |
| 2008/0021274 A1 | 1/2008 | Bayer et al. |
| 2008/0027280 A1 | 1/2008 | Fengler et al. |
| 2008/0039697 A1 | 2/2008 | Morishita |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0246920 A1 | 10/2008 | Buczek et al. |
| 2009/0012361 A1 | 1/2009 | MacKinnon et al. |
| 2009/0021739 A1 | 1/2009 | Tsujita et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0290149 A1 | 11/2009 | Roth |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0121146 A1 | 5/2010 | Sugimoto |
| 2010/0125164 A1 | 5/2010 | LaBombard |
| 2010/0157039 A1 | 6/2010 | Sugai |
| 2010/0168588 A1 | 7/2010 | Matsumoto et al. |
| 2010/0198010 A1 | 8/2010 | Cline et al. |
| 2010/0208487 A1 | 8/2010 | Li |
| 2010/0277817 A1 | 11/2010 | Durell |
| 2011/0270092 A1 | 11/2011 | Kang et al. |
| 2012/0044462 A1 | 2/2012 | Kaji |
| 2013/0237762 A1 | 9/2013 | Fengler et al. |
| 2014/0071328 A1 | 3/2014 | Miesak |
| 2014/0078378 A1 | 3/2014 | Demers et al. |
| 2014/0194687 A1 | 7/2014 | Fengler et al. |
| 2015/0184811 A1 | 7/2015 | Moore |
| 2015/0230698 A1 | 8/2015 | Cline et al. |
| 2016/0100763 A1 | 4/2016 | Fengler et al. |
| 2016/0249019 A1 | 8/2016 | Westwick et al. |
| 2017/0064257 A1 | 3/2017 | Westwick et al. |
| 2017/0064258 A1 | 3/2017 | Westwick et al. |
| 2017/0142314 A1 | 5/2017 | Moore et al. |

FOREIGN PATENT DOCUMENTS

| | | |
|---|---|---|
| CN | 201974160 U | 9/2011 |
| DE | 19535114 A1 | 3/1996 |
| DE | 19608027 A1 | 9/1996 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 1374755 A1 | 1/2004 |
| EP | 1883337 A1 | 2/2008 |
| EP | 2051603 A1 | 4/2009 |
| FR | 2671405 A1 | 7/1992 |
| JP | S-60-246733 A | 12/1985 |
| JP | S-61-159936 A | 7/1986 |
| JP | H-01-135349 A | 5/1989 |
| JP | 03-97439 A | 4/1991 |
| JP | 03-97441 A | 4/1991 |
| JP | 03-97442 A | 4/1991 |
| JP | 05-115435 A | 5/1993 |
| JP | 06-125911 A | 5/1994 |
| JP | H-07-155285 A | 6/1995 |
| JP | H-07-155286 A | 6/1995 |
| JP | H-07-155290 A | 6/1995 |
| JP | H-07-155291 A | 6/1995 |
| JP | H-07-155292 A | 6/1995 |
| JP | H-07-204156 A | 8/1995 |
| JP | H-07-222712 A | 8/1995 |
| JP | H-07-250804 A | 10/1995 |
| JP | H-07-250812 A | 10/1995 |
| JP | H-07-327913 A | 12/1995 |
| JP | H-08-126605 A | 5/1996 |
| JP | 08-140928 A2 | 6/1996 |
| JP | 08-140929 A2 | 6/1996 |
| JP | H-08-224208 A | 9/1996 |
| JP | H-08-224209 A | 9/1996 |
| JP | H-08-224210 A | 9/1996 |
| JP | H-08-224240 A | 9/1996 |
| JP | H-08-252218 A | 10/1996 |
| JP | H-09-19408 A | 1/1997 |
| JP | 09-066023 A2 | 3/1997 |
| JP | 09-070384 A2 | 3/1997 |
| JP | H-10-127563 A | 5/1998 |
| JP | H-10-151104 A | 6/1998 |
| JP | 10-201707 A2 | 8/1998 |
| JP | 10-225427 A2 | 8/1998 |
| JP | H-10-201700 A | 8/1998 |
| JP | H-10-225426 A | 8/1998 |
| JP | H-10-243915 A | 9/1998 |
| JP | H-10-243920 A | 9/1998 |
| JP | H-10-308114 A | 11/1998 |
| JP | H-10-309281 A | 11/1998 |
| JP | H-10-309282 A | 11/1998 |
| JP | H10-321005 A | 12/1998 |
| JP | H-10-328129 A | 12/1998 |
| JP | H-11-47079 A | 2/1999 |
| JP | 11-089789 A2 | 4/1999 |
| JP | 11-104059 A | 4/1999 |
| JP | 11-104060 A | 4/1999 |
| JP | 11-104061 A | 4/1999 |
| JP | H-11-104070 A | 4/1999 |
| JP | H-11-113839 A | 4/1999 |
| JP | H-11-155812 A | 6/1999 |
| JP | H-11-244220 A | 9/1999 |
| JP | H-11-332819 A | 12/1999 |
| JP | 2000-504968 A | 4/2000 |
| JP | 2000-245693 A | 9/2000 |
| JP | 2000-354583 A | 12/2000 |
| JP | 2001-078205 A | 3/2001 |
| JP | 2002-000560 A | 1/2002 |
| JP | 2002-049302 A | 2/2002 |
| JP | 2002-244122 A | 8/2002 |
| JP | 2003-045210 A | 2/2003 |
| JP | 2004-024611 A | 1/2004 |
| JP | 2004-094043 A | 3/2004 |
| JP | 2004-163902 A | 6/2004 |
| JP | 2004-520105 A | 7/2004 |
| JP | 2004-247156 A | 9/2004 |
| JP | 2004-289545 A | 10/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |

(56) References Cited

FOREIGN PATENT DOCUMENTS

| | | | |
|---|---|---|---|
| JP | 2005-058620 | A2 | 3/2005 |
| JP | 2005-080819 | A2 | 3/2005 |
| JP | 2005-081079 | A2 | 3/2005 |
| JP | 2005-292404 | A | 10/2005 |
| JP | 2006087764 | A * | 4/2006 |
| JP | 2006-525494 | A | 11/2006 |
| JP | 2007-029453 | A | 2/2007 |
| JP | 2007072392 | A * | 3/2007 |
| JP | 2007-089840 | A | 4/2007 |
| JP | 2010-117442 | A | 5/2010 |
| JP | 2011-500921 | A | 1/2011 |
| JP | 2011-528918 | A | 12/2011 |
| JP | 5231625 | B2 | 7/2013 |
| JP | 5859578 | B2 | 2/2016 |
| RU | 99592 | U1 | 11/2010 |
| WO | WO-93/04648 | A1 | 3/1993 |
| WO | WO-94/13191 | A1 | 6/1994 |
| WO | WO-95/26673 | A2 | 10/1995 |
| WO | WO-98/24360 | A1 | 6/1998 |
| WO | WO-99/01749 | A1 | 1/1999 |
| WO | WO-99/53832 | A1 | 10/1999 |
| WO | WO-00/42910 | A1 | 7/2000 |
| WO | WO-00/54652 | A1 | 9/2000 |
| WO | WO-02/07587 | A2 | 1/2002 |
| WO | WO-02/50518 | A2 | 6/2002 |
| WO | WO-03/059159 | A2 | 7/2003 |
| WO | WO-03/059159 | A8 | 7/2003 |
| WO | WO-2006/116847 | A1 | 11/2006 |
| WO | WO-2008/011722 | A1 | 1/2008 |
| WO | WO-2009/033021 | A2 | 3/2009 |
| WO | WO-2016/055837 | A1 | 4/2016 |

OTHER PUBLICATIONS

Alfano, R.R. et al. (Oct. 1987). "Fluorescence Spectra From Cancerous and Normal Human Breast and Lung Tissues," *IEEE Journal of Quantum Electronics* QE-23(10):1806-1811.

Andersson-Engels, S. et al. (Mar. 1989). "Tissue Diagnostics Using Laser Induced Fluorescence," *Ber. Bunsenges Physical Chemistry* 93(3):335-342.

Bhunchet, E. et al. (Apr. 2002). "Fluorescein Electronic Endoscopy: A Novel Method for Detection of Early Stage Gastric Cancer Not Evident to Routine Endoscopy," *Gastrointestinal Endoscopy* 55(4):562-571.

Dawson, J.B. et al. (Jul. 1980). "A Theoretical and Experimental Study of Light Absorption and Scattering by In Vivo Skin," *Phys. Med. Biol.* 25(4):695-709.

Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.

Georgakoudi, I et al. (Apr. 2005). "Characterization of Dysplastic Tissue Morphology and Biochemistry in Barrett's Esophagus using Diffuse Reflectance and Light Scattering Spectroscopy," *Techniques in Gastrointestinal Endoscopy* 7(2):100-105.

Hung, J. et al. (1991). "Autofluorescence of Normal and Malignant Bronchial Tissue," *Lasers in Surgery and Medicine* 11(2):99-105.

Török, B. et al. (May 1996). "Simultane digitale Indocyaningrün- und Fluoreszeinangiographie (Simultaneous Digital ICG and Fluorescein Angiography)," *Klin Monatsbl Augenheilkd* 208(5):333-336, (with English Translation of the Introduction only).

Chinese Office action dated Jul. 29, 2016 for application No. 2012800222843 filed on Mar. 8, 2012, eight pages.

Chinese Office action dated Nov. 24, 2015 for application No. 2012800222843 filed on Mar. 8, 2012, sixteen pages.

European Extended Search Report dated Jul. 17, 2014, for EP Application No. 09721252.6 filed on Mar. 18, 2009; eleven pages.

European Extended Search Report dated Sep. 20, 2013, for EP Application No. 08706262.6 filed on Jan. 23, 2008, five pages.

European Office Action dated Dec. 3, 2015, for EP Application No. 08706262.6 filed on Jan. 23, 2008; fifteen pages.

European Office Action dated Nov. 19, 2015, for EP Application No. 07 785 001.4, filed on Jul. 30, 2007, four pages.

European Office Action dated Nov. 3, 2015 for EP Patent Application No. 12754208.2 filed Oct. 4, 2013, four pages.

European Office Action dated Sep. 29, 2015, for EP Application No. 09721252.6 filed on Mar. 18, 2009; five pages.

European Supplemental Search Report dated Oct. 1, 2014 for EP Application No. 12754208.2 filed on Mar. 8, 2012, five pages.

European Supplemental Search Report dated Oct. 9, 2013, for European Patent Application No. 06721854.5, filed on May 4, 2005, six pages.

Extended European Search Report dated Jan. 24, 2012 for EP Application No. 07 785 001.4, filed on Jul. 30, 2007, seven pages.

Final Office Action dated Apr. 24, 2015 for U.S. Appl. No. 12/933,512, filed Nov. 24, 2010, nineteen pages.

Final Office Action dated Jul. 23, 2008, for U.S. Appl. No. 11/122,267, six pages.

Final Office Action dated Jun. 18, 2015, for U.S. Appl. No. 14/154,177, eight pages.

Final Office Action dated Jun. 5, 2014, for U.S. Appl. No. 12/761,462, fourteen pages.

Final Office Action dated May 11, 2011, for U.S. Appl. No. 11/412,715, eight pages.

Final Office Action dated May 21, 2012, for U.S. Appl. No. 11/964,330; twelve pages.

Final Office Action dated Nov. 24, 2009, for U.S. Appl. No. 11/009,965, fourteen pages.

Final Office Action dated Mar. 22, 2016 for U.S. Appl. No. 14/873,842, filed Oct. 2, 2015, eighteen pages.

International Preliminary Report on Patentability dated Feb. 3, 2009, for International Application No. PCT/CA2007/001335 filed on Jul. 30, 2007, five pages.

International Preliminary Report on Patentability dated Nov. 6, 2007, for International Application No. PCT/CA2006/000669, filed on Apr. 27, 2006, nine pages.

International Preliminary Report on Patentability dated Sep. 21, 2010, for International Application No. PCT/US2009/037506, filed on Mar. 18, 2009, seven pages.

International Search Report dated Aug. 3, 2006, for International Application No. PCT/CA2006/000669, filed on Apr. 27, 2006, three pages.

International Search Report dated Aug. 3, 2012, for International Application No. PCT/IB2012/000601, filed on Mar. 8, 2012, three pages.

International Search Report dated Dec. 7, 2007, for International Application No. PCT/CA2007/001335, filed on Jul. 30, 2007, two pages.

International Search Report dated Jan. 21, 2002, for International Application No. PCT/US2001/022198, filed on Jul. 13, 2001, three pages.

International Search Report dated Jul. 22, 2009, for International Application No. PCT/US09/37506, filed on Mar. 18, 2009, two pages.

International Search Report dated May 13, 2008 for Intentional Application No. PCT/CA2008/00015, filed on Jan. 8, 2008, one page.

Invitation to Pay additional Fees and, where Applicable, Protest Fee, dated Dec. 22, 2016 for International Application No. PCT/CA2016/051315, filed on Nov. 10, 2016, two pages.

Japanese Final Office Action dated Aug. 2, 2013, for Japanese Patent Application No. 2008-509275, filed on Apr. 27, 2006, four pages.

Japanese Notice of Allowance dated Nov. 28, 2016 for Japanese Patent Application No. 2015-245598, filed on Mar. 8, 2012, six pages.

Japanese Office Action dated Apr. 20, 2012, issued in counterpart Japanese Application No. 2011-500921, filed Mar. 18, 2009, four pages.

Japanese Office Action dated Apr. 3, 2015 in Japanese Application No. 2013-058356, filed Mar. 18, 2009, four pages.

Japanese Office Action dated Feb. 17, 2012, for Japanese Patent Application No. 2008-509275, filed on Apr. 27, 2006, six pages.

(56) References Cited

OTHER PUBLICATIONS

Japanese Office Action dated Jul. 22, 2014 for Japanese Patent Application No. 2013-557187 filed Mar. 8, 2012, seven pages.
Japanese Office Action dated Mar. 9, 2015 for Japanese Patent Application No. 2013-557187, filed Mar. 8, 2012, five pages.
Japanese Office Action dated Nov. 11, 2011, for Japanese Patent Application No. 2009-521077, filed on Jul. 30, 2007, four pages.
Japanese Office Action dated Sep. 14, 2012, for Japanese Patent Application No. 2008-509275, filed on Apr. 27, 2006, seven pages.
Japanese Office Action dated Sep. 19, 2014, for Japanese Patent Application No. 2013-246636, filed on Apr. 27, 2006, six pages.
Japanese Office dated Dec. 26, 2012 for Japanese Patent Application No. 2011-500921, filed on Mar. 18, 2009, two pages.
Japanese Office Action dated May 26, 2014 in Japanese Patent Application No. 2013-058356, filed on Mar. 18, 2009, w/Concise Explanation of the Relevance, three pages.
Korean Decision of Refusal Action dated Aug. 30, 2016 for patent application No. 10-2015-7033310 filed on Mar. 8, 2012, seven pages.
Korean Office Action dated Aug. 20, 2015 for patent application No. 20137026479 filed on Mar. 8, 2012.
Korean Office Action dated Dec. 8, 2015 for patent application No. 20157033310 filed on Mar. 8, 2012, seven pages.
Korean Notice of Allowance dated Jan. 2, 2017 for Korean Application No. 10-2015-7033310, filed on Nov. 20, 2015, three pages.
Non Final Office Action dated Apr. 2, 2009, for U.S. Appl. No. 11/009,965, thirteen pages.
Non Final Office Action dated Aug. 16, 2013, for U.S. Appl. No. 12/761,462, ten pages.
Non Final Office Action dated Aug. 16, 2013, for U.S. Appl. No. 12/761,523, nine pages.
Non Final Office Action dated Dec. 10, 2010, for U.S. Appl. No. 11/412,715, ten pages.
Non Final Office Action dated Dec. 14, 2011, for U.S. Appl. No. 11/412,715, eight pages.
Non Final Office Action dated Feb. 3, 2010, for U.S. Appl. No. 11/626,308; eleven pages.
Non Final Office Action dated Jan. 2, 2008, for U.S. Appl. No. 11/122,267, five pages.
Non Final Office Action dated Jan. 20, 2016, for U.S. Appl. No. 14/629,473, fifteen pages.
Non Final Office Action dated Jul. 17, 2003, for U.S. Appl. No. 09/905,642, six pages.
Non Final Office Action dated Jul. 2, 2013 for U.S. Appl. No. 12/933,512, filed Nov. 24, 2010, twelve pages.
Non Final Office Action dated Jun. 1, 2007, for U.S. Appl. No. 10/899,648, seven pages.
Non Final Office Action dated Jun. 20, 2008, for U.S. Appl. No. 11/009,398, fifteen pages.
Non Final Office Action dated Jun. 23, 2010, for U.S. Appl. No. 11/009,965, fifteen pages.
Non Final Office Action dated Jun. 27, 2014 for U.S. Appl. No. 13/415,561, filed Mar. 3, 2012, fourteen pages.
Non Final Office Action dated Jun. 9, 2011, for U.S. Appl. No. 11/830,323, five pages.
Non Final Office Action dated May 18, 2004, for U.S. Appl. No. 10/050,601, eight pages.
Non Final Office Action dated Nov. 23, 2009, for U.S. Appl. No. 11/969,974, seven pages.
Non Final Office Action dated Nov. 5, 2014, for U.S. Appl. No. 13/930,225; six pages.
Non Final Office Action dated Oct. 23, 2013 for U.S. Appl. No. 13/415,561, filed Mar. 8, 2012, ten pages.
Non Final Office Action dated Oct. 7, 2011, for U.S. Appl. No. 11/964,330; ten pages.
Non Final Office Action dated Sep. 12, 2014, for U.S. Appl. No. 14/154,177, four pages.
Non Final Office Action dated Sep. 6, 2016 for U.S. Appl. No. 14/873,842, filed Oct. 2, 2015, seven pages.
Non Final Office Action with Restriction Requirement dated Mar. 4, 2011, for U.S. Appl. No. 11/830,323, nine pages.
U.S. Appl. No. 15/348,664, titled "Systems and Methods for Illumination and Imaging of a Target."
Design U.S. Appl. No. 29/562,795, filed Apr. 28, 2016, titled "Device for Illumination and Imaging of a Target."
Notice of Allowance dated Dec. 30, 2016, for U.S. Appl. No. 14/873,842, filed Oct. 2, 2015, eleven pages.
Notice of Allowance dated Apr. 7, 2004, for U.S. Appl. No. 09/905,642, six pages.
Notice of Allowance dated Aug. 26, 2004, for U.S. Appl. No. 10/050,601, eight pages.
Notice of Allowance dated Aug. 6, 2015, for U.S. Appl. No. 13/853,656, seven pages.
Notice of Allowance dated Dec. 10, 2012, for U.S. Appl. No. 11/964,330; seven pages.
Notice of Allowance dated Feb. 25, 2010, for U.S. Appl. No. 11/969,974, four pages.
Notice of Allowance dated Jan. 2, 2008, for U.S. Appl. No. 10/899,648, three pages.
Notice of Allowance dated Jun. 25, 2015, for U.S. Appl. No. 12/933,512, filed Nov. 24, 2010 fourteen pages.
Notice of Allowance dated Mar. 22, 2013, for U.S. Appl. No. 11/964,330; eight pages.
Notice of Allowance dated Mar. 28, 2016, for U.S. Appl. No. 13/853,656 eight pages.
Notice of Allowance dated May 18, 2015, for U.S. Appl. No. 13/930,225; nine pages.
Notice of Allowance dated Nov. 23, 2015, for U.S. Appl. No. 13/853,656, seven pages.
Notice of Allowance dated Oct. 10, 2014, for U.S. Appl. No. 12/761,462, ten pages.
Notice of Allowance dated Oct. 5, 2007, for U.S. Appl. No. 10/899,648, six pages.
Notice of Allowance dated Sep. 10, 2013, for U.S. Appl. No. 11/412,715, eight pages.
Notice of Allowance dated Sep. 14, 2012, for U.S. Appl. No. 11/830,323, eight pages.
Russian Office Action—Decision to Grant dated Aug. 19, 2016 for Russian Patent Application No. 2013144845/07, filed on Mar. 8, 2012, thirteen pages.
Supplemental Notice of Allowability dated Mar. 10, 2005, for U.S. Appl. No. 10/050,601, five pages.
Written Opinion of the International Searching Authority dated Aug. 3, 2006, for International Application No. PCT/CA2006/000669, filed on Apr. 27, 2006, eight pages.
Written Opinion of the International Searching Authority dated Dec. 7, 2007, for International Application No. PCT/CA2007/001335, filed on Jul. 30, 2007, four pages.
Japanese Notice of Allowance dated Jan. 5, 2017 in Japanese Patent Application No. 2015-238784, filed on Dec. 7, 2015, six pages.
Canadian Examiner's Report for Registration of an Industrial Design dated Feb. 1, 2017 for Canadian Application No. 171282, filed on Oct. 27, 2016, two pages.
Chinese Third Office Action dated Mar. 14, 2017 for Chinese Patent Application No. 201280022284.3, filed on Nov. 7, 2013, seven pages.
European Communication pursuant to Rules 70(2) and 70a(2) EPC and Reference to Rule 39(1) EPC dated Jan. 23, 2017 for European Application No. 16186321.2 filed on Aug. 30, 2016, two pages.
European Communication under Rule 71(3) EPC dated Nov. 25, 2016 for EP Application No. 08706262.6 filed on Aug. 21, 2009, eight pages.
European Search Report and Written Opinion dated Dec. 21, 2016 for European Application No. 16186321.2 filed on Aug. 30, 2016, nine pages.
International Search Report and Written Opinion dated Apr. 24, 2017, for International Application No. PCT/CA2017/050083, filed on Jan. 26, 2017, seven pages.
International Search Report and Written Opinion of the International Searching Authority dated Feb. 10, 2017, for International Application No. PCT/CA2016/051315 filed on Nov. 10, 2016, thirteen pages.

(56) References Cited

OTHER PUBLICATIONS

U.S. Non Final Office Action dated Feb. 1, 2017, for U.S. Appl. No. 14/860,687, filed Sep. 21, 2015, sixteen pages.
U.S. Non Final Office Action dated Jan. 26, 2017, for U.S. Appl. No. 15/343,034, filed Nov. 3, 2016, seventeen pages.
U.S. Non Final Office Action dated Jan. 27, 2017, for U.S. Appl. No. 15/343,038, filed Nov. 3, 2016, fifteen pages.
U.S. Appl. No. 15/584,405 titled "Imaging System for Combine Full-Color Reflectance and Near-Infrared Imaging," filed May 2, 2017.

* cited by examiner

FULL SPECTRUM LED ILLUMINATOR HAVING A MECHANICAL ENCLOSURE AND HEATSINK

REFERENCE TO RELATED APPLICATIONS

This application is a continuation of U.S. patent application Ser. No. 14/658,869, filed Mar. 16, 2015, which is a continuation of U.S. patent application Ser. No. 13/415,561, filed Mar. 8, 2012, now U.S. Pat. No. 8,979,301, which claims the benefit of provisional Application No. 61/450,360, filed Mar. 8, 2011, the entire contents of which are incorporated herein by reference.

BACKGROUND OF THE INVENTION

The present disclosure relates to an illumination system, in particular for endoscopy, and more particularly a full spectrum illumination system using light-emitting diodes (LED) and/or semiconductor lasers.

Illumination systems for endoscopy, microscopy and similar optical imaging applications have for many years utilized arc lamp or halogen technology as the light source of choice. More recently, various forms of solid state light sources such as light emitting diodes or diode lasers have been introduced for use in some of these imaging applications. Due to the output brightness or output spectrum limitations of these solid state light sources, the use of LEDs and/or laser diodes has, until recently, been limited to optical imaging applications where low light levels are sufficient or where narrow spectrum illumination is required/desired.

Achieving sufficiently bright, full visible spectrum illumination with solid state light sources has remained challenging for a number of reasons.

a) Firstly, LED technology has been improving, but started far behind that of lamp technology in terms of total light output. Increasingly higher light outputs are now available, but light from a single phosphor-coated ("white") LED, for example, is still orders of magnitude below that of an arc lamp.

b) Alternatively light from multiple, different colored (e.g. red, green and blue) LEDs can be combined using dichroic mirrors to "source" emitting over a wide spectral range. The imaging applications mentioned above, however, generally require coupling light into liquid, fiberoptic, or rod lens light guides. Such optical light guides typically have both a small physical aperture with dimensions of a few mm across and a constrained/limited numerical aperture (NA). Moreover, etendue considerations rapidly constrain the practical implementation of such combined source illumination systems.

c) Should the etendue considerations with a multiple different colored LED arrangement be overcome by a suitable arrangement of sources and dichroics with optical path lengths that are carefully equalized, then other implementation issues arise with respect to effective cooling and cost.

Finally, although output brightness of red and blue LEDs has reached levels at which they can produce light with a brightness substantially equivalent to that of the red and blue portions of an arc lamp or a halogen lamp spectrum, the output of green LEDs tends to be substantially less than the green light produced by lamps.

It would therefore be desirable and advantageous to address this problem and to obviate other prior art shortcomings by providing a cost-effective and reliable illuminator utilizing solid state light sources to produce a bright, color balanced, broad spectrum visible light output that may be effectively coupled to an optical light guide. It would also be desirable to include in such illuminator and in the resulting light emission, other light sources for UV or NIR illumination (e.g. for fluorescence excitation of tissue).

SUMMARY OF THE INVENTION

According to one aspect of the present disclosure, an illuminator is disclosed which utilizes solid state light sources to produce a bright, color balanced, broad-spectrum, visible light output.

According to one advantageous feature of the disclosure, the illuminator may contain multiple high power LED light sources that span the visible spectrum (e.g. from 400-700 nm). These LED light sources are separately powered and controlled. The light produced by these LEDs is combined into a single beam using either mirrors or dichroic filters appropriately wavelength matched to the LED light output. The combined light may then be coupled into an optical light guide using an appropriate optical element such as a high (e.g. >0.5) NA lens.

According to one advantageous feature of the disclosure, the illuminator may include LED light sources housed in discrete high thermal conductivity packages. The LED dies may be edge-emitting or surface emitting and they may be packaged in single or multi-die configurations.

According to one advantageous feature of the disclosure, the illuminator may contain a combination of red, green and blue LED light sources. Alternatively or in addition, one or more of these LED light sources may have other hues of the visible spectrum, including violet, yellow, amber/orange LEDs, as required or desirable for the application (e.g. in the endoscope). Alternatively, or in addition, a single LED package may contain any combination of these color dies.

According to one advantageous feature of the disclosure, to increase the green component of the emitted light and provide a more color balanced output, the illuminator may contain in addition to red and blue LED light sources at least two green LED light sources, such as a long wavelength green and a short wavelength green. The peak wavelengths and bandwidth of the two green LEDs is carefully selected to ensure that the combining optics produce maximum net green light output. In one embodiment the long wavelength green may have a peak wavelength at ~530 nm and an approximate FWHM bandwidth of +/−40 nm and the short wavelength green may have a peak wavelength at ~515 nm and an approximate FWHM bandwidth of +/−37 nm.

According to one advantageous feature of the disclosure, the LED light sources may be mounted on a heat sink in good thermal contact with a single heat spreader plate. The spreader plate may be a metal having high thermal conductivity, such as copper, aluminum, iron, diamond, gold or silver and the like. The spreader plate may be mounted on or integral with a passive cooling system, such as a finned heat sink or a heat pipe, or an active cooling system, such as a thermoelectric cooler (TEC) or liquid cooler. Thermal contact between the LEDs and the plate may be provided by, for example, soldering or with the application of a thermally conductive compound, such as Type 120 Silicon Thermal Joint Compound (Wakefield Thermal Solutions, New Hampshire). This mounting arrangement and cooling structure optimizes both cost/complexity of the assembly and cooling efficiency and therefore also the lifetime/reliability of the solid state source.

According to one advantageous feature of the disclosure, the LED light sources may be mounted on a plane which is common to the planar surface of the heat sink on the single heat spreader plate, with the optical path length increasing with wavelength, e.g. the red LED has longest optical path, the blue LED has shortest optical path. LED light source is positioned at or near the focal point of a compound collector group consisting of an aspheric lens (e.g., Newport KPA040-C, Irvine, Calif.), which collects the light from each LED light source. The collection efficiency of the aspheric lens may be enhanced by a field lens mounted between the LED and the aspheric lens. The aspheric lens projects a nearly collimated light beam from the LED onto a mirror or a dichroic filter (e.g. Semrock FF670-SDi01-25×36, Rochester, N.Y.) positioned to reflect light at a right angle relative to the light projected by the aspheric lens into the combined light beam path. The dichroic filter is designed to reflect substantially all light at or above the wavelength of the LED emission and transmits the light of all shorter wavelengths. The power and position of each aspheric lens and the power and position of any field lens is adjusted as required for each LED to accommodate the differences in optical path lengths. In this way, the etendue constraints with a linear arrangement of light sources can be managed and the capacity of the high NA lens in coupling the combined beam of light into an optical light guide can be maximized.

According to one advantageous feature of the disclosure, all optical elements not directly attached to the LED light sources (including all remaining collector lenses, reflective and dichroic mirrors, and collimating/condensing lenses) may be mounted in a mating mechanical enclosure. The enclosure may be fabricated from a single block of material such as aluminum, or similar material and may be machined or may be cast and machined as a single element. The mechanical enclosure may also be composed of multiple elements individually fabricated (e.g. machined) and assembled. The enclosure has a linear array of input ports matching the linear pattern of LED sources on the heat spreader plate—e.g., one input port for each LED light source and a single output port. Once all optical components are mounted in the enclosure, the plate with the LED light sources is assembled to the enclosure input ports and a shutter that seals the exit aperture in the absence of a light guide is mounted placed on the output port. The enclosure is consequently fully sealed and the optical elements are protected against the ingress of dust and other contaminants.

According to one advantageous feature of the disclosure, the illuminator may utilize a design without lenses and have instead polished reflective surfaces that propagate the light emitted by the LEDs. The light can then, as before, be combined using dichroic filters, with the combined light being coupled into the optical light guide, by means of reflective surfaces.

According to one advantageous feature of the disclosure, the illuminator may also contain other light sources, such as one or more diode lasers, that are coupled into the combined optical path. In one embodiment, the diode lasers may be fiber coupled NIR lasers that emit in the 800-820 nm wavelength range suitable for fluorescence excitation of, for example, indocyanine green (ICG) or other NIR excited fluorescence agent. Alternatively or in addition, one or more of the fiber coupled diode lasers may produce 830 nm NIR light for purposes of mimicking the fluorescence of ICG. The NIR light emitted by the lasers may be coupled into the optical path by introducing an additional dichroic mirror that reflects NIR but transmits shorter wavelengths into the LED optical path. Alternatively, or in addition, the illuminator may contain one or more UV diode lasers for tissue autofluorescence excitation. These lasers may be coupled into the blue LED channel or directly coupled into the combined beam channel before the blue LED dichroic filter. The illuminator may also contain high powered NIR or UV LEDs instead of diode lasers.

The system also provides for imaging a conjugate plane from the collector group onto the light guide (i.e. fit a round cone to the light guide).

BRIEF DESCRIPTION OF THE DRAWINGS

Other features and advantages of the present invention will be more readily apparent upon reading the following description of currently preferred exemplified embodiments of the invention with reference to the accompanying drawing, in which.

DETAILED DESCRIPTION OF THE EMBODIMENTS

Figure 1:
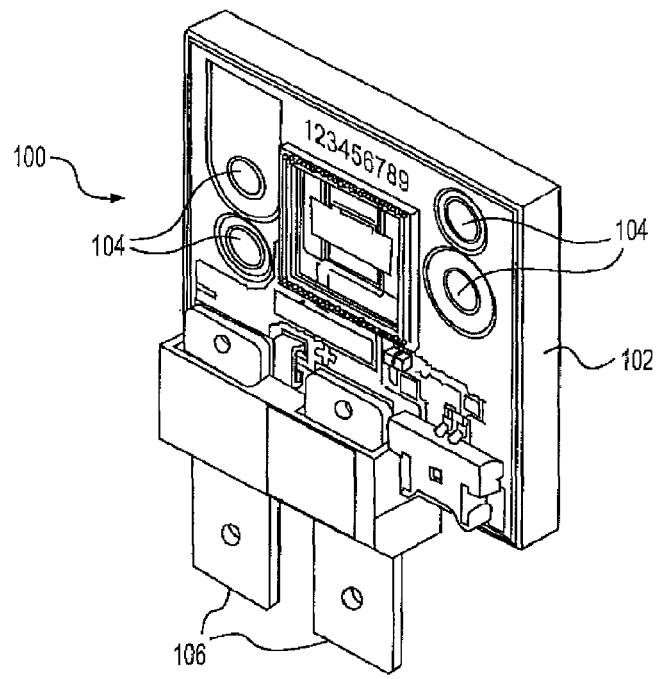
FIG. 1 shows an LED package with a highly thermally conductive substrate.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Figure 2:
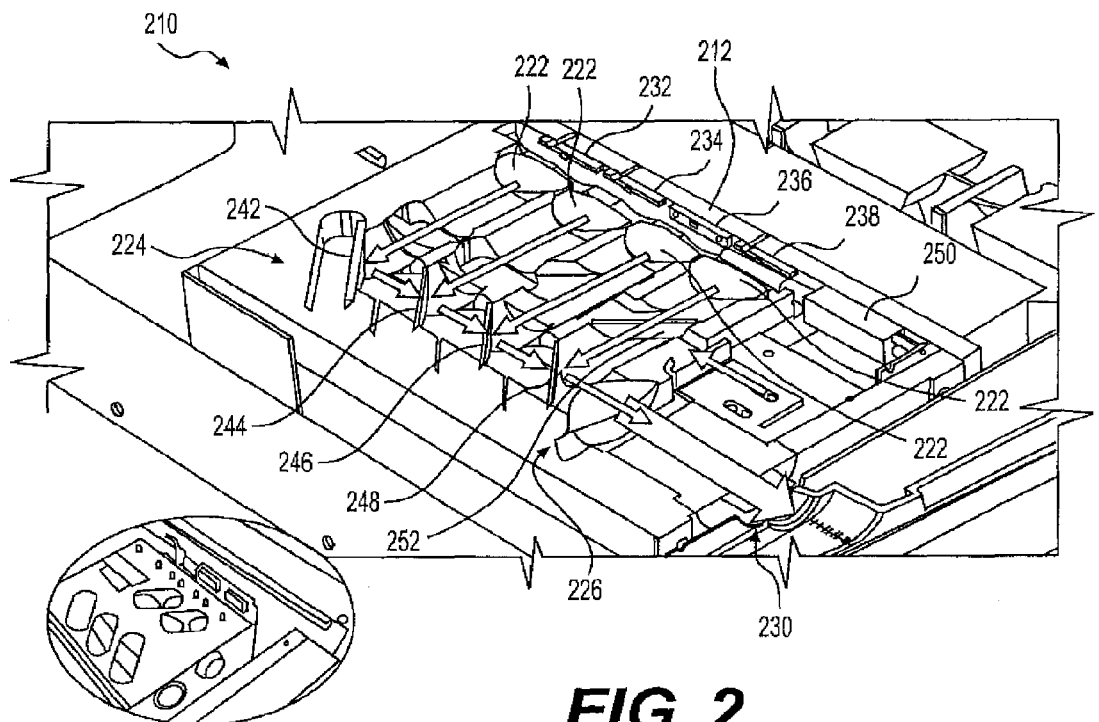
FIG. 2 shows in a cut-away view an illuminator with a linear array of LEDs arranged on a heat spreader, with collection, combining and condensing optics.

Turning now to the drawing, and in particular to FIG. 1, there is shown an LED package 100 including a substrate 102 with high thermal conductivity having mounting holes 104 for attachment to a heat spreader 212 shown in FIG. 2. The LED package also includes electrical terminals 106 for supplying electric power to the LEDs.

FIG. 2 shows in a cut-away view an illuminator 210 with a linear array of LEDs 232, 234, 236, 238 arranged on the heat spreader 212, with collector optics 222, combining optics 242, 244, 246, 248, and condensing optics 226. The LEDS 212 are arranged with increasing optical path lengths from a combined light output port 230. Collector optics 222, such as an aspheric lens and optionally a field lens, may be placed in front of each LED. The light from the red LED 232 is reflected at a 90° angle by a mirror 242. Additional dichroic mirrors 244, 246, 248 are placed in the combined beam path between this mirror 242 and the combined light output port 230. These dichroic mirrors 244, 246, 248 are designed to reflect, in the listed order, at a 90° angle light emitted by the exemplary long wavelength green LED 234 (peak wavelength at ~530 nm and approximate FWHM bandwidth of +/−40 nm), the exemplary short wavelength green LED 236 (peak wavelength at ~515 nm and approximate FWHM bandwidth of +/−37 nm), and the exemplary blue LED 238 (peak wavelength at ~460 nm and approximate FWHM bandwidth of +/−25 nm), while transmitting the wavelengths already present in the propagating combined beam, i.e., red, red+long green, red+long green+short green.

According to some exemplary embodiments, optical elements not directly attached to the LED light sources, for example, collector lenses, reflective and dichroic mirrors, and collimating/condensing lenses, may be mounted in a mating mechanical enclosure 224. The enclosure may be fabricated from a single block of material such as aluminum, or similar material, and may be machined or may be cast and machined as a single element. The mechanical enclosure may also be composed of multiple elements individually fabricated (e.g. machined) and assembled. The enclosure 224 has a linear array of input ports matching the linear pattern of LED sources 232, 234, 236, 238 on the heat spreader plate 212 e.g., one input port for each LED light source—and a single output port. Once all optical components are mounted in the enclosure 224, the heat spreader plate 212 with the LED light sources 232, 234, 236, 238 is assembled to the enclosure input ports.

The illuminator 210 may contain one or more other light sources, such as a diode laser 250, that are coupled into the combined optical path. The diode laser 250 may be a fiber-coupled NIR laser that emits in the 800-820 nm wavelength range suitable for fluorescence excitation of, for example, indocyanine green (ICG) or other NIR-excited fluorescence agent. Alternatively or additionally, a fiber-coupled diode laser may produce 830 nm NIR light for purposes of mimicking the fluorescence of ICG. As shown in FIG. 2, the NIR light emitted by the laser 250 may be coupled into the optical path by introducing an additional dichroic mirror 252 that reflects NIR but transmits shorter wavelengths into the LED optical path. Alternatively or additionally, the illuminator 210 may contain one or more UV diode lasers for tissue autofluorescence excitation. The aforementioned lasers may be coupled into the channel of the blue LED 238 or directly coupled into the combined beam channel before the blue LED dichroic filter 248. The illuminator 210 may also contain high powered NIR or UV LEDs instead of diode lasers.

Figure 3:
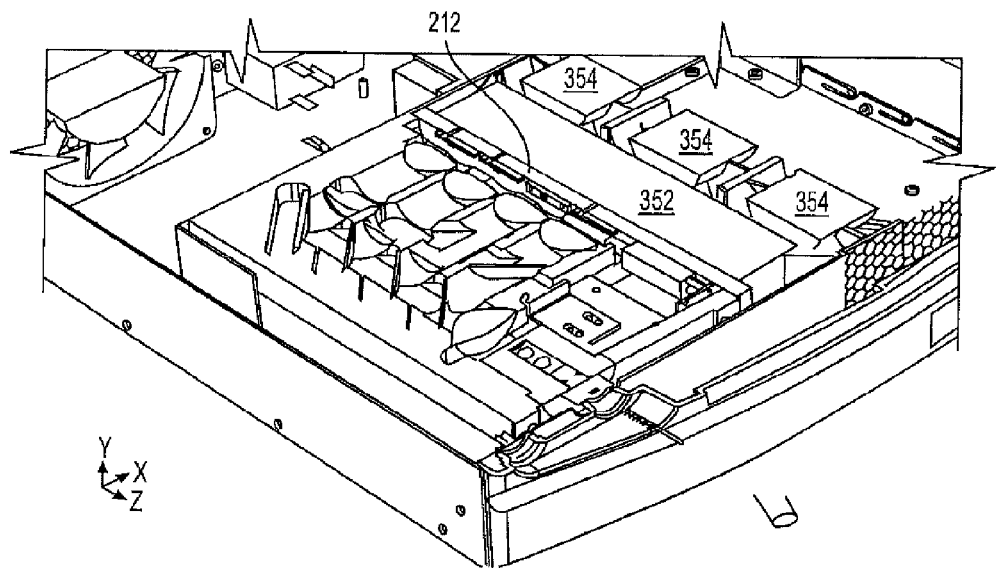
FIG. 3 shows in a cut-away view an illuminator with a linear array of LEDs arranged on a heat spreader, with heat exchanger and fans.

FIG. 3 shows schematically the illuminator in a cut-away view with the linear array of LEDs 232, 234, 236 on heat spreader 212, the LED-Laser heat exchanger (heat sink) 352, and the LED-Laser heat exchanger fans 354.

Figure 4:
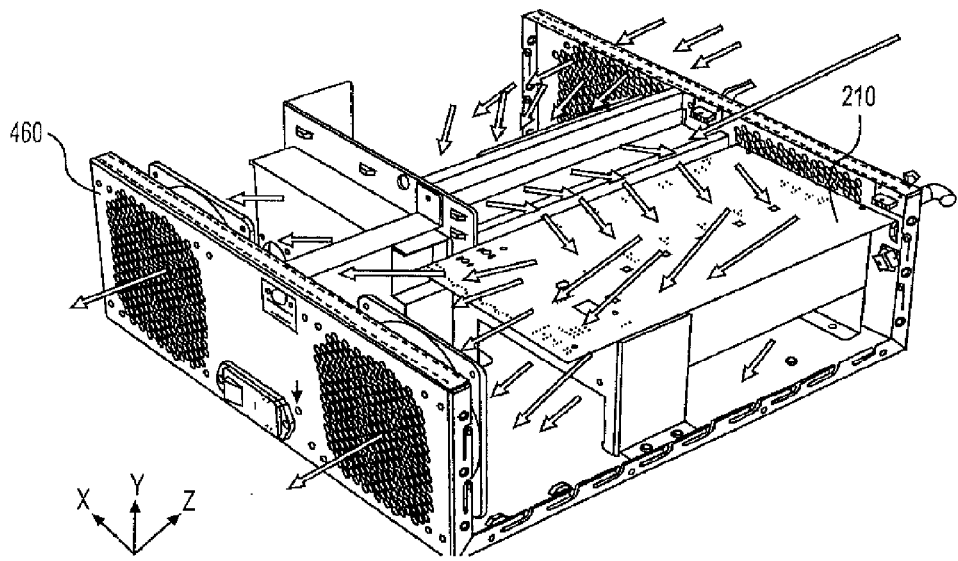
FIG. 4 shows an exemplary air flow pattern of the illuminator in an enclosure.

FIG. 4 shows schematically an exemplary air flow pattern around the illuminator 210 in the enclosure 460. FIG. 4 is a perspective view that differs from the view of FIG. 3, as shown by the X-Y-Z axis.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed is:

1. An apparatus for providing a light output to an optical guide for illumination of an object to be imaged, the apparatus comprising:
    a plurality of solid state light-emitting sources each of which are independently powered and independently controlled, each light-emitting source emitting light at a wavelength that is different from a wavelength emitted by the other light-emitting sources;
    a heat sink configured to thermally couple the plurality of solid state light-emitting sources and provide conduction of heat generated by the plurality of solid state light-emitting sources, wherein the heat sink comprises a heat spreader plate having a planar surface and each of the solid-state light-emitting sources is mounted to the planar surface to orient each of the solid-state light-emitting sources along a common optical plane;
    optical elements configured to collect, collimate, and combine the emissions from the plurality of solid state light-emitting sources into a combined beam of light to be optically coupled to a light guide at an output of the apparatus; and
    a mechanical enclosure comprising a linear array of input ports matching a linear pattern of the light-emitting sources on the planar surface, wherein at least some of the optical elements are not directly attached to the light-emitting sources and the at least some of the optical elements not directly attached to the light-emitting sources are mounted in the mechanical enclosure and the heat spreader plate is configured to be assembled to the enclosure so as to seal the enclosure,
    wherein light emitted from each of the light-emitting sources travels an optical path length from the respective light-emitting source to the output, the optical path lengths from the light-emitting sources to the output varying based on the wavelength of the light emitted from the respective light-emitting source.

2. The apparatus of claim 1, wherein the heat sink comprises a passive cooling system.

3. The apparatus of claim 2, wherein the passive cooling system is a finned heat sink or a heat pipe.

4. The apparatus of claim 1, wherein the heat sink comprises an active cooling system.

5. The apparatus of claim 4, wherein the active cooling system is a thermoelectric cooler or a liquid cooler.

6. The apparatus of claim 1, wherein the solid state light-emitting sources comprise light emitting diodes and diode lasers.

7. The apparatus of claim 1, wherein the optical elements comprise a field lens and an aspheric lens configured to collect and collimate the emission from each of the plurality of solid state light-emitting sources.

8. The apparatus of claim 1, further comprising a dichroic filter configured to couple the collimated emission from each of the plurality of solid state light-emitting sources into the combined beam of light directed along a common path to an output port.

9. The apparatus of claim 1, wherein the optical elements are arranged such that the optical path length of each of the plurality of solid state light-emitting sources increases as the wavelength increases.

10. The apparatus of claim 1, wherein the optical elements are arranged such that the optical path length of each of the plurality of solid state light-emitting sources increases as the wavelength decreases.

11. The apparatus of claim 1, wherein the common optical plane comprises focal points of a compound collector group.

12. The apparatus of claim 1, wherein the heat spreader plate comprises copper, aluminum, iron, diamond, gold or silver.

13. The apparatus of claim 1, wherein the heat sink comprises a passive cooling system or an active cooling system and the passive or active cooling system is arranged on a side of the heat spreader plate opposite the planar surface.

* * * * *